United States Patent [19]

Kirsch

[11] 4,179,810
[45] Dec. 25, 1979

[54] DEVICE FOR MILLING SLOTS IN A JAWBONE FOR MOUNTING AN ENDOSSAL DEVICE

[76] Inventor: Axel Kirsch, Scharnhauser Str. 3, 7024 Bernhausen, Fed. Rep. of Germany

[21] Appl. No.: 845,819

[22] Filed: Oct. 27, 1977

[30] Foreign Application Priority Data

Mar. 31, 1977 [DE] Fed. Rep. of Germany ....... 2714321

[51] Int. Cl.² ...................... A61C 13/00; A61B 17/32; A61F 5/04; B26B 7/00
[52] U.S. Cl. .................................. 433/75; 128/305; 128/92 E; 30/276; 433/82; 433/165; 433/176
[58] Field of Search .................. 32/10 A, 46, 47, 48, 32/49, 50, 57, 58, 59, 40 R, 1, 23, 29; 128/305, 317, 310, 305.1, 305.3, 305.5, 92 E, 92 EB, 92 G; 90/12 R; 125/13; 83/488, 489, 887, 743, 745; 30/371, 372, 276, 291; 144/42, 253 J; 29/78

[56] References Cited

U.S. PATENT DOCUMENTS

| | | | |
|---|---|---|---|
| 823,167 | 6/1906 | Green | 32/29 |
| 1,173,902 | 2/1916 | Vansco | 83/745 |
| 1,230,696 | 6/1917 | Filotico | 125/13 R |
| 2,685,738 | 8/1954 | Leff | 32/59 |
| 3,127,886 | 4/1964 | Miller | 125/13.9 |
| 3,719,186 | 3/1973 | Merig, Jr. | 128/305.1 |
| 3,798,771 | 3/1974 | Edelman | 32/10 A |
| 3,945,117 | 3/1976 | Beaver | 128/305 |
| 3,951,564 | 4/1976 | Montgomery | 83/488 |
| 3,992,780 | 11/1976 | Herskovits | 32/10 A |
| 4,004,581 | 1/1977 | Heimke et al. | 128/305 |
| 4,116,200 | 9/1978 | Braun et al. | 128/305 |

*Primary Examiner*—Louis G. Mancene
*Assistant Examiner*—Michael J. Foycik
*Attorney, Agent, or Firm*—Allegretti, Newitt, Witcoff & McAndrews

[57] ABSTRACT

A milling device for cutting a circular arcuate slot in a human jawbone, which slot is adapted to receive an endossal implant for mounting a denture. The device has a circular sawblade mounted in a housing comprising two parts. One part is adapted to slide into the other and carries the rotatably mounted sawblade. The other part serves as a guide to control the direction and distance the blade moves with respect to the bone being cut, thereby providing an accurately dimensioned slot for receiving the implant.

15 Claims, 7 Drawing Figures

DEVICE FOR MILLING SLOTS IN A JAWBONE FOR MOUNTING AN ENDOSSAL DEVICE

BACKGROUND AND SUMMARY OF THE INVENTION

The invention relates to a device or tool for producing a slot in a human jawbone for receiving, with precise fit, an endossal implant for fastening a denture.

The invention relates furthermore to such an implant, having a post from which two lateral bearing arms extend, which in the direction of the axis of the post have a large extension, and transversely to the axis of the post have a slight extension. The lower edge of each arm constitutes a contact surface at the jawbone.

From prior art German Specification DT-OS 2,505,914 a device is known in which a milling cutter with a cylindrical bearing surface is utilized, having a guide slot which serves as a template for guidance. Since the length of the bearing surface is limited, the guidance is poor.

Since cylindrical millers can function only to a shallow working depth, it is necessary, in the milling of a slot, to utilize a larger number of special cylindrical millers of varying length, and to frequently change the millers. Because the millers can tilt they may break off. Hence the operational time is prolonged. In the case of cylindrical millers, furthermore, the flushing of the cutting surfaces is difficult.

The primary object of the invention is to provide a device which can be simply operated, in which the danger of tool breakage is reduced, the carrying away of the removed bone material and the flushing of cutting surfaces are simplified, and in particular a very precise slot with completely plane lateral surfaces and smooth and precise terminal edges is assured.

The object of the invention is accomplished by means of a circular saw having a circularly curved sawblade, positioned in a housing which partially surrounds the sawblade, and including means for the guidance of the sawblade in a radial direction from the housing.

The sawblade utilized in the device constructed according to the invention, makes possible the production of a slot during the course of an operation without exchanging the cutting tools. Thereby the operational time is on the whole reduced to about one-third of the time previously required. That means a lessening of the danger of infection and an improvement in the prospects for the in-healing of the implant. Precise guidance of the sawblade is assured by its rotational mounting in the housing, so that no lateral grooves are produced in the slot being cut. Additionally the contour of the edge of the slot is precisely defined, so that a correspondingly shaped implant rests exactly with its contact edges against the edges of the slot. In use the sawblade will seldom break, so that even in the case of brief bending loads a loss of the tool cannot occur. In addition to this the sawblade itself, with a corresponding shaping, effects an independent guidance through its lateral surfaces. Since the teeth of the sawblade continuously leave the saw-slot for a certain time, an excellent removal of the sawdust results. The removal of sawdust from the teeth is effected by simple flushing means, which simultaneously removes the flushing medium which flows through the teeth into the slot.

The circularly curved contour of the peripheral edges of the slot is in many cases advantageous, because it adapts itself, particularly in the area of the side teeth, to the shape of the mandibular canal. This is especially advantageous where there is a lower bone height over the mandibular canal and little available space.

In one embodiment of the invention the free part of the sawblade is constantly protected by the upper part of the housing, while the lower part of the housing, through contact surfaces, assures an exact positioning of the saw in relation to the jawbone; particularly, without impairment by the gums, a precise depth of the saw cut is assured.

In another embodiment of the invention sliding rods between the housing parts protect the sawblade, when the housing parts are widely spaced from each other. A fitting pin projecting therefrom fixes the second housing part against lateral movement with respect to the jawbone, so that the forces generated by the saw are transmitted directly to the jawbone, without lateral movements of the housing. Therefore the sawblade can rise freely without binding.

According to an additional feature a stub tube for supplying flushing fluid to the teeth of the sawblade is provided.

Another embodiment renders possible a housing of lesser width in the plane of the sawblade, which in practice is limited to that of the sawblade. For this reason the device can be utilized in small gaps between teeth. A further modification of this embodiment consists of a member having a slot for mounting the sawblade, and bearings on both sides of the slot for rotatably mounting the axle of the sawblade. Positioning bearings on both sides of the axle of the sawblade, improves the guidance and the resistance to wear.

Another structural feature of this embodiment consists in providing on the slide member in the area of the bearings projections extending outwardly from the saw axle, which projections slide in corresponding guide grooves on the inside of the housing. In spite of the small dimensions of the parts, there is assured exact parallel guidance in the direction the saw advances. In addition the sawblade is completely enclosed by the housing in the retracted or partially-advanced position.

In order to be able to utilize fully the advantages of the device constructed according to the invention, the enossal implant previously mentioned is characterized in that the lower edges of the bearing arms lie on a common circular line or circumference. The circularly-shaped lower edges of the implant can be produced quite precisely, and since the peripheral edges of the slot for the implant are also exactly circularly shaped, an extremely uniform positioning of the lower edges of the bearing arms of the implant is assured. This is of advantage for the in-healing process, and for the later load bearing capacity of the implant in use. According to another embodiment, the implant utilizes a base body of metal, which imparts to the implant the desirable characteristics of solidity, rigidity and ease of processing. This base body is provided with a coating, the tissue compatibility of which is greater than that of the metal itself. The material for the coating is selected with reference to high tissue compatibility, so that the implant combines the advantages of a metal implant, with the advantages of a tissue-compatible material.

A suitable coating material is aluminum oxide. This material is so hard that it is not suitable as base material for the implant. As a coating material it covers the total surface of the implant, so as to impart complete tissue compatibility thereto. Titanium oxide is also exceptionally well suited as a coating material. The preferred coating consists of a mixture of 60% Al$_2$O$_3$ and 40% TiO$_2$. With the aid of the drawings and the following examples the invention should be fully clarified.

DESCRIPTION OF THE PREFERRED EMBODIMENTS

Figure 1:
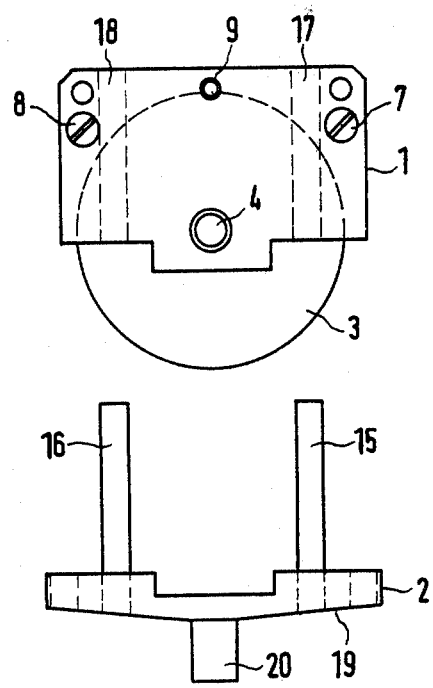
FIG. 1 is a front elevational view of one embodiment of a device or cutting tool constructed in accordance with the invention.
Figure 2:
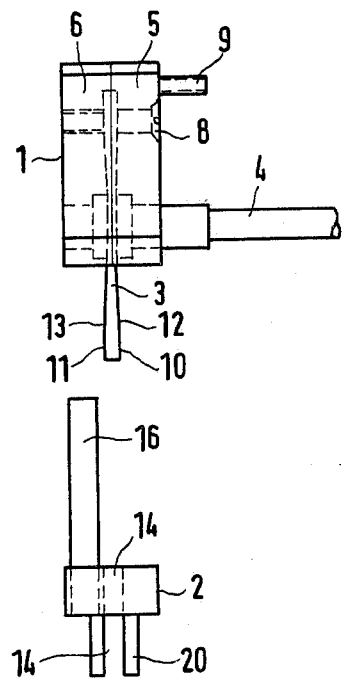
FIG. 2 is a side view of the device of FIG. 1.

The cutting device shown in FIGS. 1 and 2 consists of two housing parts 1 and 2. The housing part 1 surrounds the upper half of sawblade 3, the axle 4 of which is mounted in the housing part 1. Housing part 1, for the purpose of more simple production, has two halves 5 and 6, connected by means of screws 7 and 8. In the half 5 of the housing part 1 there is located a stub tube 9, for attaching a hose for flushing fluid. As can be readily observed from FIG. 1, the stub tube 9 is directed to the tooth area of the sawblade 3, so that the water entering into housing part 1, in the form of a jet, flushes particles from the teeth. The water is furthermore carried by the teeth into the slot for rinsing purposes.

As can be observed from FIG. 2, the thickness of the sawblade 3 is reduced toward the axle 4 to minimize friction between the sawblade and the lateral walls of the milled slot being cut in the jawbone. Furthermore it is to be observed that lateral surfaces 10 and 11 of the teeth on the circumference of the sawblade (not shown in detail in the drawing) lie in a radial plane, as do the annular areas 12 and 13 of the lateral surfaces beneath the teeth. These lateral surfaces 11, 13 and 10,12 provide a certain independent guidance of the sawblade in the sawed slot.

The second housing part 2 is in effect an extension or cut off portion of housing part 1, as can be observed from FIGS. 1 and 2. It has a slot 14, the width of which is somewhat larger than that of the sawblade 3, and through which the sawblade extends.

Rods 15 and 16 extend upwardly from part 2 and are adapted to slide in bores 17 and 18 in housing part 1. For a better understanding of the structure the housing portions 1 and 2 in FIGS. 1 and 2 are shown separated from each other, rather than with the rods 15, 16 inserted in the bores 17, 18.

On the lower side of the housing part 1 there is located a contact surface 19, for contacting the upper side of a jawbone. A fitting pin 20 extends from the contact surface 19 through which the slot 14 extends. The pin is to be inserted into a previously bored hole in the jawbone. Thereby the total device for maximizing the sawing strength of the sawblade 3 is aligned with the slot 14.

When utilizing the device, a fitting hole is first of all drilled into the jawbone, corresponding to the dimensions of the fitting pin 20. Then the fitting pin 20 is inserted into this hole until the contact surface 19 lies against the jawbone. The sawblade 3 is propelled by means of a handpiece attached to the axle 4. Flushing fluid is supplied through the stub pipes 9. Through force on the housing part 1, the sawblade 3 is moved against the jawbone, and the cutting is initiated. The forward movement of the saw is continued until the housing part 1 contacts the housing part 2, whereby the depth of the sawed slot is precisely delimited.

Figure 3:
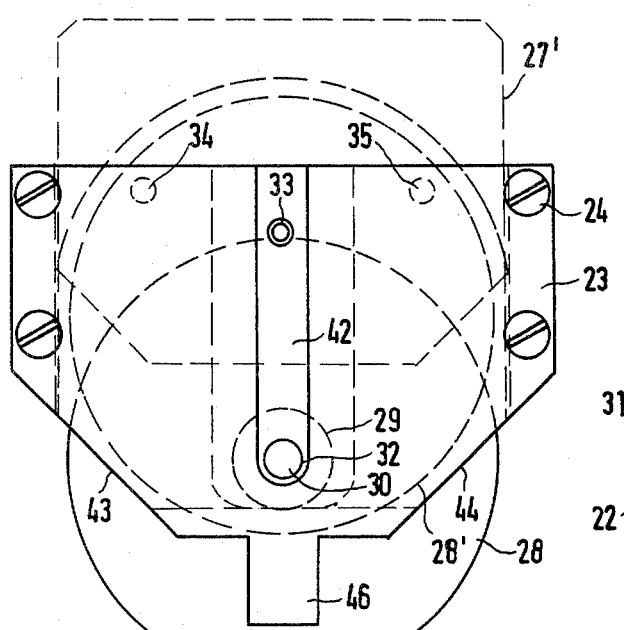
FIG. 3 is a front elevational view of an additional embodiment looking in the direction of the axle of the sawblade.
Figure 5:
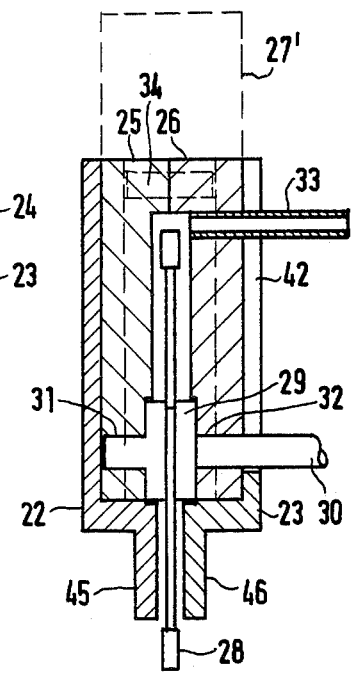
FIG. 5 is a vertical section through FIG. 3 at the axle of the sawblade.
Figure 4:
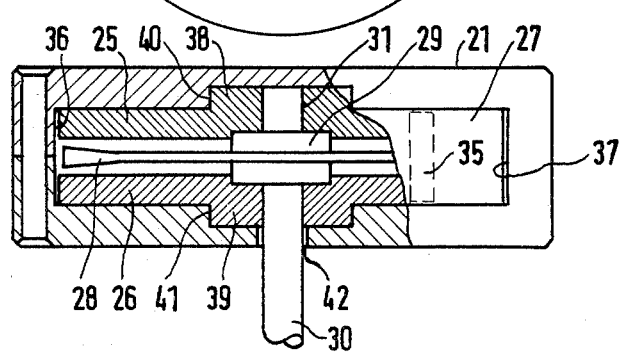
FIG. 4 is a top view of the device of FIG. 3, with portions cut away.

The example of embodiment represented in FIGS. 3 to 5 is described with simultaneous reference to all three figures.

A housing 21 consists of two halves 22 and 23 which are fastened together by screws 24. Between the halves 22 and 23 there is a clear space in which is located a slide member 27 which is divided into two halves 25 and 26, which slide is shiftably carried in the clear interior space of the housing 21. In FIGS. 3 and 5 it may be seen that the slide is in its run-in position, in which it lies entirely within the interior space of the housing 21 and a saw blade 28 is thrust forward to the farthest extent.

The sawblade 28 is held by a driving collar 29 located on an axis of rotation 30 which on either side of the driving collar is carried in the bearings 31 and 32 of the halves 25 and 26 of the slide 27. It may be seen from FIG. 5 that the two halves 25 and 26 form between them a slot in which the saw blade 28 rotates. In the half 26 of the slide 27 there is mounted a pipe connection 33 by means of which a flushing fluid can be directed upon the teeth of the saw blade 28. The two halves 25 and 26 are held together by the pins 34 and 35.

It may be seen from FIG. 4 that the slide 27 with the halves 25 and 26, transversely to the direction of advance and to the direction of the axis of rotation 30 of the saw blade 23, is of smaller dimension than the opposed inner walls 36 and 37 of the housing 21. These inner walls 36 and 37 thus do not serve for guidance. Instead of this there are provided on the halves 25 and 26 projections 38 and 39 extending in the direction of feed, which slide in corresponding guide slots 40 and 41 in the housing 21. These projections 38 and 39 thus effect the specific guidance and in addition, since they lie within the region of the axis of rotation 30 they make possible a greater axial dimension for the bearings of rotation 31 and 32.

In order that the axle 30 may move freely in a forward direction, there is located in the portion 23 of the housing 21 a guide slot 42 slightly larger than the axle 30. The stub tube 33 also moves in the same slot 42.

From FIG. 3 it is to be observed that the housing 21 at its lower portion where the sawblade 28 exits is provided with bevels 43 and 44, so that the lower contour of the housing 21 corresponds approximately to the circumference of the retracted sawblade, indicated by a dotted line 28'. In a solid line the sawblade 28 is represented at its most advanced position. When the sawblade is located at the position indicated by the line 28', then the slide 27 is located in the position indicated by a broken line 27'.

At the lower edge of both halves 25 and 26 of the housing, there are located projections 45 and 46 in the form of circular segments or arcs, which are insertable into a previously milled slot in the jawbone, hence the round contour.

Figure 6:
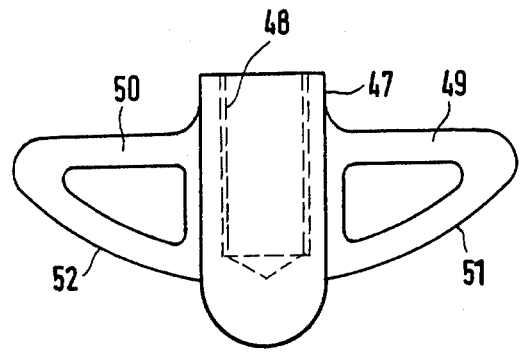
FIG. 6 is a front view of an implant according to the invention.
Figure 7:
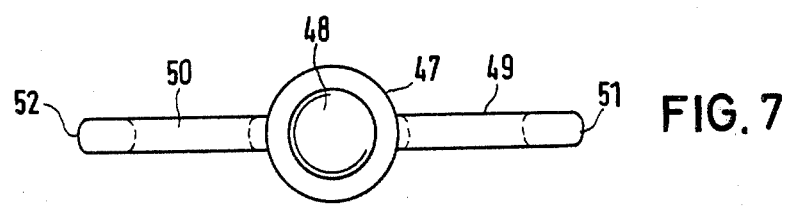
FIG. 7 is a top view of the implant of FIG. 6.

FIGS. 6 and 7 show an implant for insertion in a slot, which is cut with a device shown in the other figures.

The implant is represented, in the interest of clarity, on a large scale.

From a central post 47, having a threaded bore 48 for fastening a denture, there extends lateral bearing arms 49 and 50, whose lower edges 51 and 52 lie on a common circular line, which corresponds to the outer circumference of the sawblade 28, and thus is precisely fitted to it.

As observable from FIG. 7, the lower edges 51 and 52 constitute contact surfaces for the transmission to the jawbone of forces acting on the implant.

What is claimed is:

1. A surgical tool for cutting a slot in a jawbone for implantation of an endossal implant to which a denture may be firmly fastened comprising, in combination:
   (a) a housing-slide member comprising two parts, the second part of which has a bearing surface for bearing against a jawbone;
   (b) a sawblade for cutting a precisely dimensioned slot in the jawbone rotatably mounted on the first part of the housing-slide member;
   (c) guide means connecting the first and second parts of the housing-slide member which permits the parts to slide with respect to each other and further permits the sliding of the sawblade radially outwardly of the second part of the housing-slide member; and
   (d) means for maintaining the bearing surface of the second part of the housing-slide member at a site on the jawbone.

2. The tool of claim 1 in which the sawblade is circular.

3. The tool of claim 2 in which the thickness of the sawblade diminishes from the circumference to the center.

4. The tool of claim 2 in which the first part of the housing-slide member covers all but a segment constituting less than half of the sawblade.

5. The tool of claim 2 in which the housing-slide member has surfaces where the sawblade exits which approximate the circumference of the sawblade in contour.

6. The tool of claim 1 in which the second part of the housing-slide member has a surface opposed to the bearing surface which serves as a stop for limiting the movement of the first part of the housing-slide member.

7. The tool of claim 6 in which the first part of the housing-slide member has a surface which abuts the opposed surface of the second part of the housing-slide member and has the same contour as said opposed surface of the second part.

8. The tool of claim 1 in which the guide means comprises a pair of rods mounted on the second part of the housing-slide member and a pair of bores in the first part of the housing-slide member for slidably receiving the rods.

9. The tool of claim 1 in which the means for maintaining the bearing surface of the second part of the housing-slide member at a site on the jawbone comprises a fitting pin projecting from said bearing surface and insertable in a fitting hole in the jawbone.

10. The tool of claim 9 in which the fitting pin is aligned with the sawblade and is split by a slit through which the sawblade may pass.

11. The tool of claim 1 including a tube for supplying flushing fluid to the sawblade entering the first housing-slide member.

12. The tool of claim 11 in which the tube is axially mounted with respect to the sawblade and is oriented so as to deliver flushing fluid directly to teeth of the sawblade.

13. The tool of claim 1 in which the guide means comprises a pair of opposed projections on the first part of the housing-slide member extending in the direction of feed and a pair of opposed glide slots in the second part of the housing-slide member to slidably receive the projections.

14. The tool of claim 13 in which the housing-slide member is divided into two halves along the plane of the sawblade.

15. A surgical tool for cutting a slot in a jawbone for implantation of an enossal implant to which a denture may be firmly fastened comprising, in combination:
   (a) a housing-slide member comprising two parts, the second part of which has a bearing surface for bearing against a jawbone;
   (b) a circular sawblade for cutting a precisely dimensioned slot in the jawbone rotatably mounted on the first part of the housing-slide member and entirely covered by said first part except for a segment constituting less than half of the sawblade; and
   (c) guide means connecting the first and second parts of the housing-slide member which permits the parts to slide with respect to each other and further permits the sliding of the sawblade radially outwardly of the second part of the housing-slide member.

* * * * *